(12) United States Patent
Bin

(10) Patent No.: US 9,400,238 B2
(45) Date of Patent: Jul. 26, 2016

(54) SHEARING FORCE TEST DEVICE

(75) Inventor: Weixiong Bin, Shenzhen (CN)

(73) Assignee: WEIXIONG BIN, Shenzhen (CN)

( * ) Notice: Subject to any disclaimer, the term of this patent is extended or adjusted under 35 U.S.C. 154(b) by 304 days.

(21) Appl. No.: 14/123,495

(22) PCT Filed: Jun. 4, 2012

(86) PCT No.: PCT/CN2012/076433
§ 371 (c)(1),
(2), (4) Date: Jan. 23, 2014

(87) PCT Pub. No.: WO2012/171437
PCT Pub. Date: Dec. 20, 2012

(65) Prior Publication Data
US 2014/0157909 A1    Jun. 12, 2014

(30) Foreign Application Priority Data

Jun. 13, 2011 (CN) .......................... 2011 1 0157669

(51) Int. Cl.
*G01N 3/00* (2006.01)
*G01N 11/00* (2006.01)
*G01N 3/08* (2006.01)
*G01N 3/24* (2006.01)
*G01L 5/00* (2006.01)

(52) U.S. Cl.
CPC ................ *G01N 3/24* (2013.01); *G01L 5/0076* (2013.01); *G01N 2203/0296* (2013.01)

(58) Field of Classification Search
None
See application file for complete search history.

(56) References Cited

U.S. PATENT DOCUMENTS

| | | | | |
|---|---|---|---|---|
| 6,301,971 B1* | 10/2001 | Sykes | ....................... | G01N 3/00 73/827 |
| 7,997,147 B2* | 8/2011 | Sykes | ....................... | G01N 3/24 73/150 A |
| 8,424,390 B2* | 4/2013 | Lilley | ....................... | G01N 3/24 73/841 |
| 8,714,025 B2* | 5/2014 | Lilley | ....................... | G01N 3/24 73/788 |
| 2008/0190212 A1* | 8/2008 | Sykes | ....................... | G01N 3/00 73/841 |
| 2011/0277555 A1* | 11/2011 | Peecock | ................ | G01L 5/0033 73/827 |

* cited by examiner

Primary Examiner — Michael A Lyons
Assistant Examiner — Jermaine Jenkins
(74) Attorney, Agent, or Firm — CBM Patent Consulting, LLC

(57) ABSTRACT

A shearing force test device comprises a substrate mounted with an elastomer having a free end capable of moving toward or away from the substrate; the free end is connected with a test head; the elastomer is installed with two U-shaped elastic arms arranged at a distance and capable of mutually neutralizing horizontal position offsets; the free ends of the two U-shaped elastic arms are connected together; the test head is fixedly installed on the free end; the two U-shaped elastic arms are provided with the fixed end of the elastomer there between; the fixed ends of the two U-shaped elastic arms are connected together, and are fixedly connected with the substrate; and the other ends of the two U-shaped elastic arms away from the free ends are fixedly connected together via a connecting plate.

12 Claims, 5 Drawing Sheets

SHEARING FORCE TEST DEVICE

This application is the U.S. national phase of International Application No. PCT/CN2012/076433 filed 4 Jun. 2012 which designated the U.S. and claims priority to Chinese Application No. CN201110157669.8 filed 13 Jun. 2011, the entire contents of each of which are hereby incorporated by reference

FIELD OF THE INVENTION

The invention relates to a shearing force test device for testing the welding firmness of a fine pitch or ultra fine pitch semiconductor device and the conducting wire or conductor thereof.

BACKGROUND OF THE INVENTION

With the constant development of the semiconductor technology, more and more functions are integrated onto a small sized wafer substrate, and the wires laid on the wafer substrate are denser and denser. The device with 65 nm wide wires has been successfully developed at present, and the device with 45 nm wide wires will be produced in large scale finally. With the gradual popularization and application of the fine pitch or ultra fine pitch lead bonding technology, the pitch between conducting wires or conductors becomes smaller and smaller, achieving 60-40 um, and even as small as 35-30 um within a few years in the future. As a result, a chip having the same size as before has more and more powerful functions nowadays.

The conducting wire welded on a wafer usually has the diameter of 25.4 um/20 um or even thinner e.g. 18 um. And the diameter of a corresponding welded gold ball is 32 um-50 um. Those connecting wires and gold balls must be firmly and reliably welded on a weld pad on a wafer substrate. The to-be-tested welded object is too small in size, therefore the test device must precisely align the welded gold ball to be tested, and generates no alignment bias during the process after the alignment before the termination of the test, so as to ensure the accuracy of the test result.

All known test devices have a basic structure provided with a horizontally placed or vertically placed force sensor, and an implemental push cutter used for contacting and positioning a plane attached by a to-be-tested welded object for testing shearing force. By contacting the plane attached by the to-be-tested welded object via the implemental push cutter, the position of the plane attached by the to-be-tested welded object in the Z axis direction can be sensed. The position is taken as a benchmark to determine the bottom of the to-be-tested welded object, and heighten by a preset height h, e.g. 3 um, relative to the bottom of the to-be-tested welded object; and then a relative movement is conducted for testing the shearing force, thus obtaining a repeatable welding strength test value.

The U.S. Pat. No. 6,078,387 discloses a mechanism realizing contact sensing: the mechanism is provided with a main body having a horizontal double-arm cantilever beam structure; one end of the double-arm cantilever beam is fixed on a fixing block, and the other end (free end) is connected with a moving block and a probe (namely the implemental push cutter in the present patent). The free end of the double-arm cantilever beam can move freely up and down under the effect of an air bearing. Firstly of all, a photoelectric sensor is utilized to sense the displacement generated when the probe fixed on the moving block at the free end of the double-arm cantilever beam contacts the plane attached by the to-be-tested welded object; then the compressed air supply is stopped to cease the effect of the air bearing, and the elasticity of the double-arm cantilever beam is utilized to fix the moving block on the fixing block, thus realizing positioning purpose.

According to physical common sense and geometry knowledge, when the free end of the cantilever beam displaces up and down relative to the fixed end, the free end will inevitably have a horizontal displacement at the same time. That is to say, the method employing a cantilever beam structure to realize contact sensing actually has the problem of horizontal offset between fixed positions before and after the contact, such as the offset P1 as shown in FIG. 4.

Supposing that the length of the cantilever beam is L; in order to realize the above contact, the free end rotates an angle a1 after contacting a target plane; and the endpoint of the free end of the cantilever beam moves from D1 to D2, in which case the free end of the cantilever beam will inevitably have a position offset P1. According to the triangle relationship, the corresponding relationships between the position offset P1 and the rotation angle a1, the included angle a2 between the connecting line of the two displacement points and the normal line, and the cantilever beam length L can be easily obtained as follows:

$$B = 2 \times L \times \mathrm{Sin}(a1/2)$$

$$P1 = B \times \mathrm{Sin}\ a2 = 2 \times L \times \mathrm{Sin}(a1/2) \times \mathrm{Sin}(a2)$$

The specific offset caused by a specific cantilever beam structure will not be discussed herein. However, it can be affirmatively determined that the contact positioning mode using a cantilever beam structure will result in the offset between fixed contact positions, and the horizontal offset P1 (as shown in FIG. 4) between fixed contact positions may result in the dislocation between the implemental push cutter and the to-be-tested welded object; and different contact forces will cause nonlinear change of the horizontal offset P1 between fixed contact positions, thus not facilitating the control of different contact forces.

FIG. 5 vividly shows the relative sizes and relative positions of the implemental push cutter and the welded gold ball from the relative movement direction during the shearing force test process of the welded gold ball which is a fine pitch or ultra fine pitch semiconductor product. As shown in FIG. 5, in a densely arranged welded gold ball array, because the welded gold balls are arranged densely, the gap between welded gold balls is very small. The implemental push cutter shall not offset along the horizontal offset P1 direction (FIG. 5) of the fixed position aligned before the shearing force test is conducted. The position offset may cause dislocated shearing to the implemental push cutter and the welded gold ball to be tested, that is to say, the welded gold ball may be sheared incompletely and two welded gold balls may be partially sheared, thus resulting in failed test results. The problem of horizontal offset of the fixed position shall be avoided during the shearing force test of the fine pitch or ultra fine pitch semiconductor.

As a matter of course, when the cantilever beam structure is used, the rotation angle can be controlled in a very small range with various methods, so that the horizontal offset P1 of the fixed position can be reduced but cannot be avoided. And when a greater contractor force is required to confirm the contact, a greater rotation angle a1 will certainly be required, in which case the offset P1 of the fixed position will greatly increase accordingly.

In order to solve the above problem, a Chinese patent CN201382828 discloses a shearing force test device, comprising a substrate capable of moving up and down and mounted with an elastomer having a free end capable of moving towards or away from the substrate, the free end being connected with a test head; wherein the elastomer has a horizontal symmetrical structure; the free end is located on the symmetric line of the elastomer having the horizontal symmetrical structure; a pressing mechanism for fixing the test head is arranged above the test head; a gap facilitating the vertical moving of the free end and the test head connected to the free end is arranged between the free end and the substrate; after the test head is accurately positioned, the free end closely leans against the substrate under the effect of the pressing mechanism to fix the test head. The shearing force test device properly solves the problem that horizontal offset will occur to the fixed contact position during the shearing force test process. However, the device still has the problem of front and back small swaying.

BRIEF DESCRIPTION OF THE INVENTION

Aiming to overcome the above defects, the invention provides the society with a shearing force test device which not only completely eliminates the horizontal offset problem between fixed positions but also ensures to test to be more reliable and accurate.

The basic thought of the invention is to introduce into the sensor employed by the invention a mechanism capable of actively and naturally compensating inverse horizontal displacement offset, so as to reduce the offset occurred during test to the most extent in principle.

The technical solution of the invention is to design a shearing force test device comprising a substrate; the substrate is provided with an elastomer thereon capable of eliminating the offset of the fixed contact position via an active and natural reverse horizontal position offset compensation when sensing a contact; the elastomer is provided with a free end capable of moving toward or away from the substrate; the free end is connected with a test head; the elastomer comprises four elastic arms 100, 100', 200, 200', wherein the elastic arms 100, 100' are connected end to end to form a first U-shaped elastic arm, and the elastic arms 200, 200' are connected end to end to form a second U-shaped elastic arm. Please refer to FIG. 2.

The first U-shaped elastic arm formed by the elastic arms 100, 100' of the elastomer, and the second U-shaped elastic arm formed by the elastic arms 200, 200' are vertically placed at a distance. The fixed ends of the first U-shaped elastic arm and the second U-shaped elastic arm are respectively connected with a fixing block 400 disposed between the first U-shaped elastic arm and the second U-shaped elastic arm; the fixing block 400 is fixedly installed on a substrate 4; the free end parts of the first U-shaped elastic arm and the second U-shaped elastic arm are connected to form a free end 5; and the test head is fixed on the free end 5.

As an improvement of the invention, a micromotion mechanism is arranged between the free end and the substrate, wherein the micromotion mechanism yields a gap between the substrate and the free end as well as the test head connected to the free end during the process of sensing a small contact force by the test head.

As a further improvement of the invention, the micromotion mechanism comprises a sliding block and an air bearing; the sliding block is movably connected with the free end, and is flatly pressed on the substrate; the air bearing is arranged in the back of the sliding block; and the air outlet of the air bearing aligns to the back side surface of the sliding block. When the compressed air is imported, the air bearing is activated to push away the sliding block, the free end and the test head connected to the free end, and retain the three components a certain gap from the substrate; after the fixed contact position is accurately found, the compressed air is removed and the air bearing is deactivated, thus the sliding block, the free end and the test head connected to the free end are pressed back to the substrate by the elastomer, and are fixed on the substrate via a contact friction force.

As a further improvement of the invention, the micromotion mechanism is a planar rolling bearing or a linear bearing.

As a further improvement of the invention, the micromotion mechanism is provided with a magnetic body at the free end, and a coil on the substrate at a position opposing to the free end. After the coil is powered on, the magnetism generated by the coil is the same with the magnetism of the free end, and has a repulsion action on the free end, thus the free end and the test head connected to the free end are pushed away and kept a certain gap from the substrate. After the fixed contact position is accurately found, the coil is powered with a reverse current, the coil generates a magnetism attracting the magnet on the free end, thus the sliding block, the free end and the test head connected to the free end are pressed back to the substrate under the combined action of the elastomer and a magnetic force, and are fixed on the substrate via a greater contact friction force.

As a further improvement of the invention, a sensing element is adhered at a position where the elastomer strain is concentrated, the sensing element being used to sense the deformation of the elastomer and control the magnitude of the contact force so as to adapt the contact of different soft/hard surfaces.

As a further improvement of the invention, the sensing element is a strain meter or a photoelectric sensor.

As a further improvement of the invention, the elastic arm of the elastomer can be placed horizontally.

The invention employs an elastomer having horizontal position offset compensation during shearing force test process; therefore the contact point will have no horizontal offset during contact positioning. In addition, under the effect of the micromotion mechanism, the free end and the test head connected to the free end are basically in a natural falling state with no vertical friction under the effect of gravity and the elastic arm in the process of sensing a small contact force, and are maintained on the same vertical line in the process of sensing contact forces, thus satisfying the extremely precise positioning requirement during the shearing force test of the fine pitch or ultra fine pitch semiconductor.

DETAILED DESCRIPTION OF THE INVENTION

Figure 1:
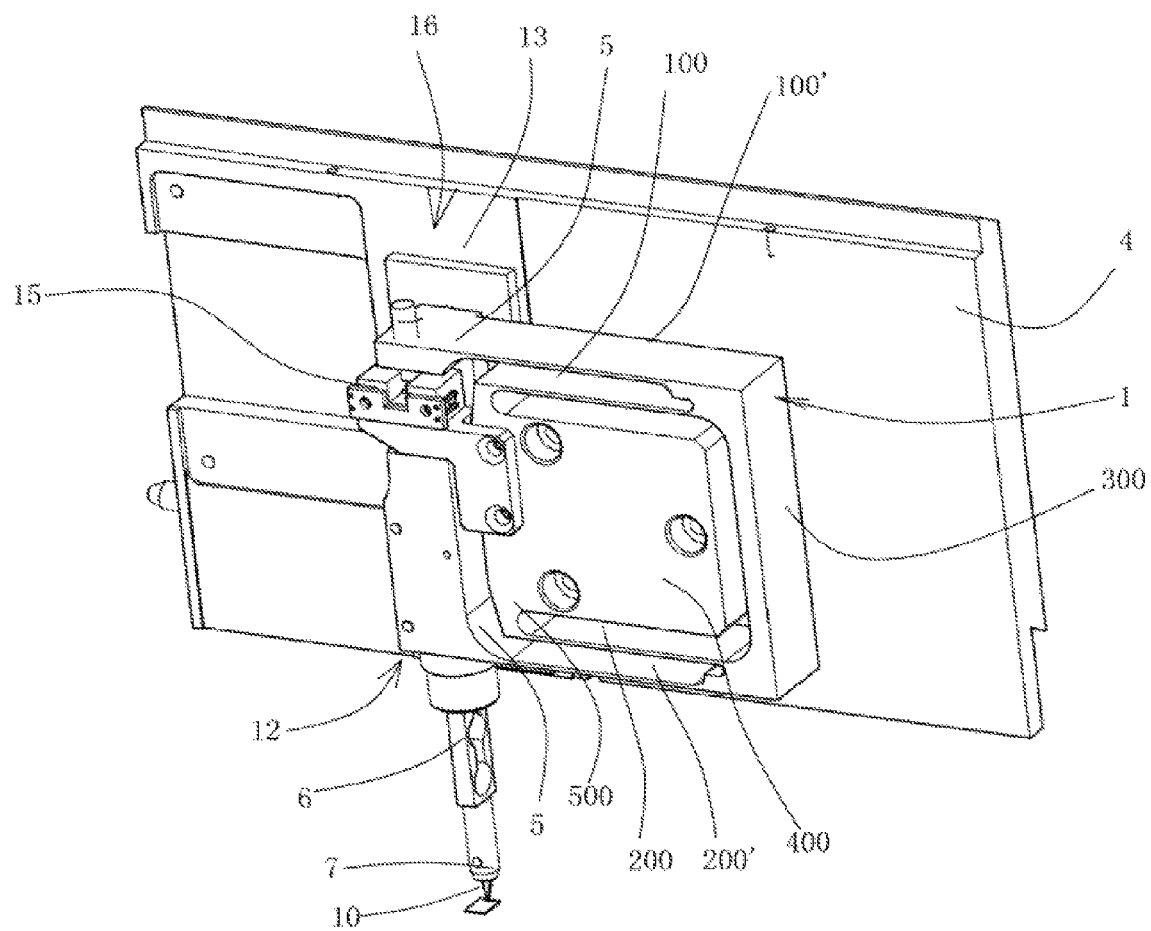
FIG. 1 is the stereoscopic structure schematic diagram of a test device according to an embodiment of the invention.
Figure 2:
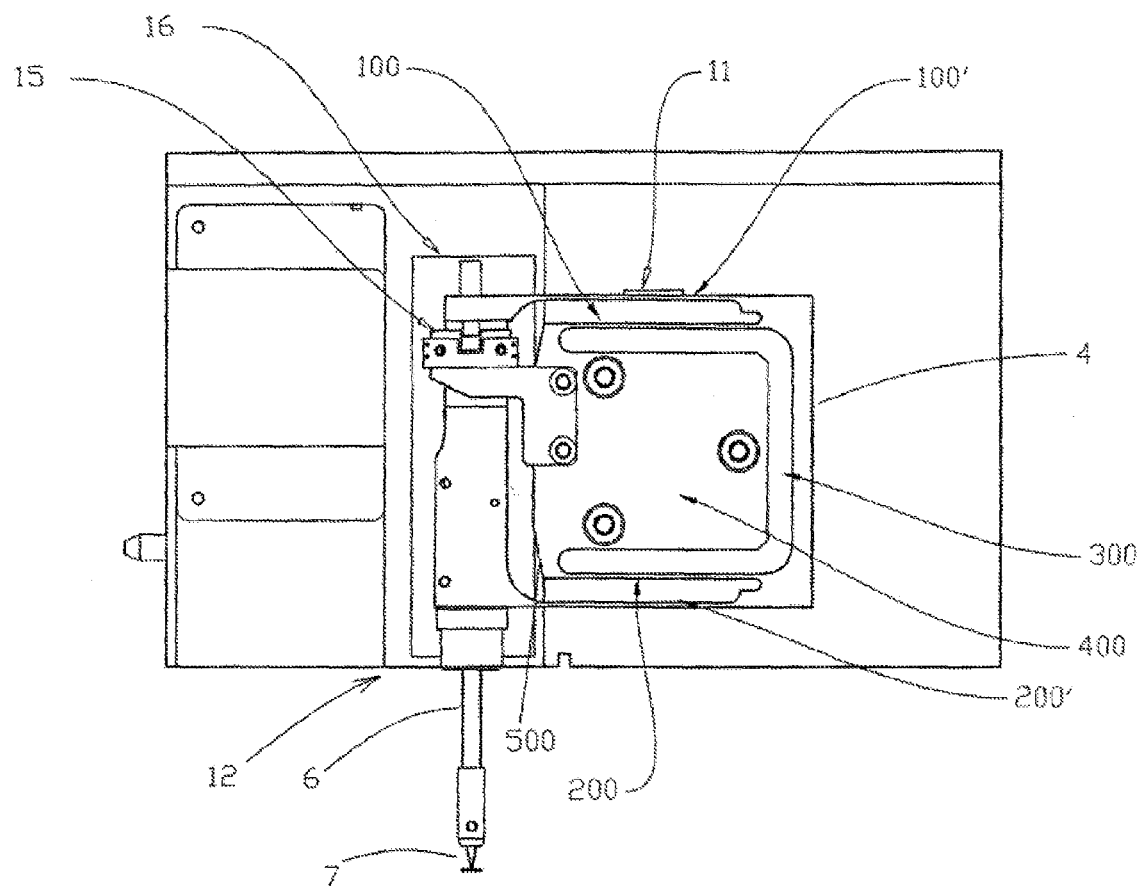
FIG. 2 is the planar structure schematic diagram of the front view of the test device as shown in FIG. 1.
Figure 3:
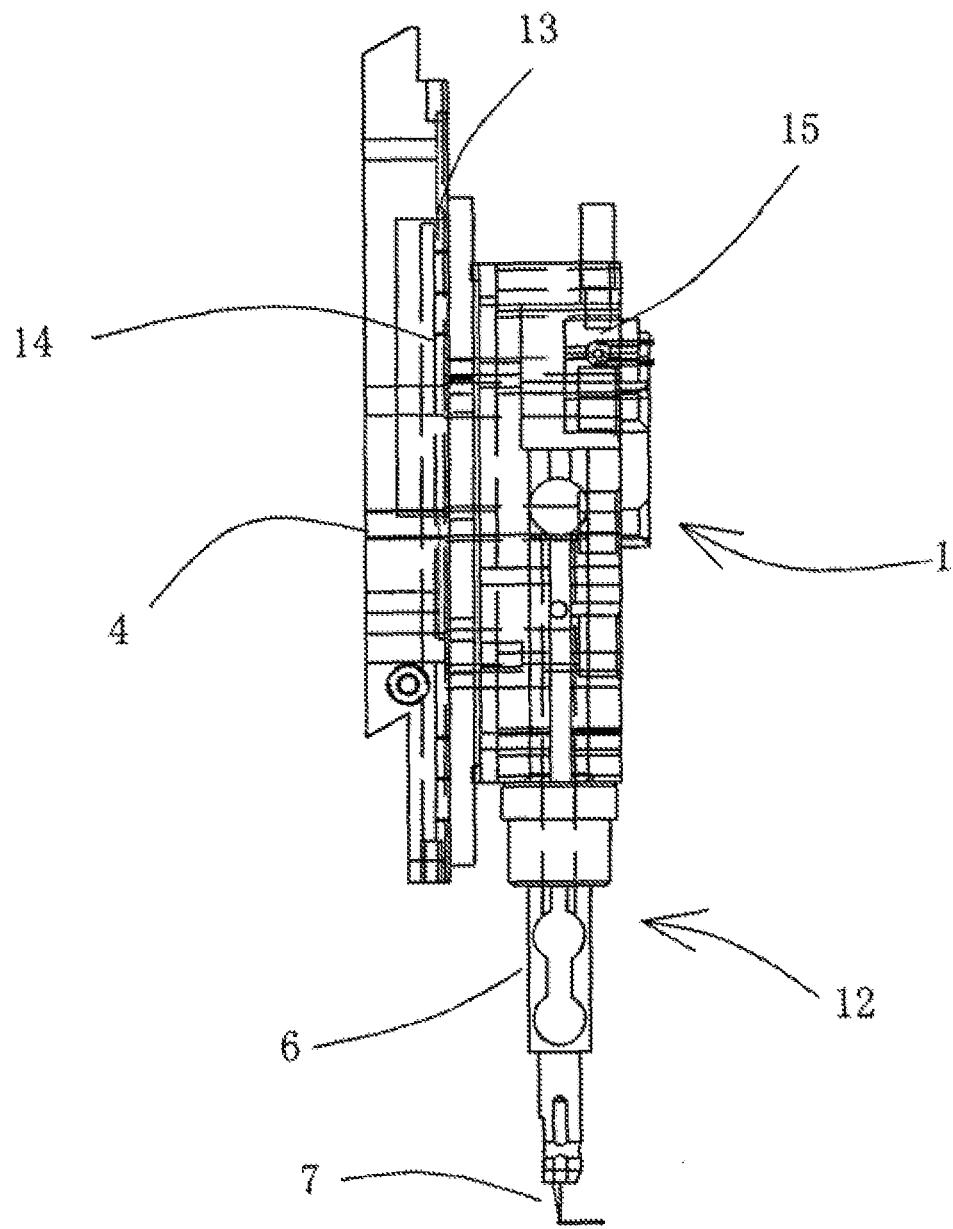
FIG. 3 is the planar structure schematic diagram of the side view of the test device as shown in FIG. 1.
Figure 4:
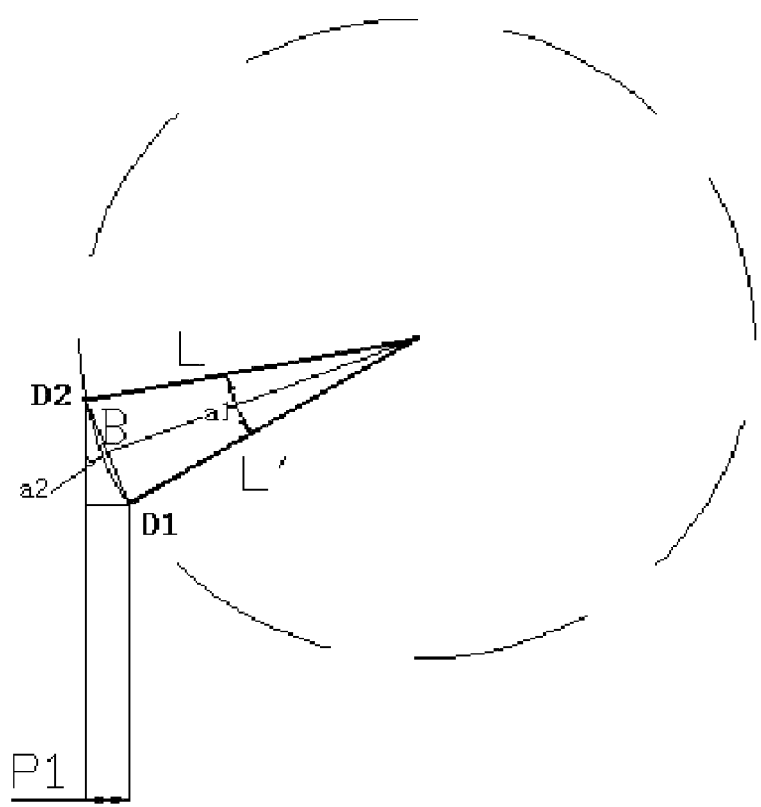
FIG. 4 is the planar structure schematic diagram of a problem in principle that an existing test device has.
Figure 5:
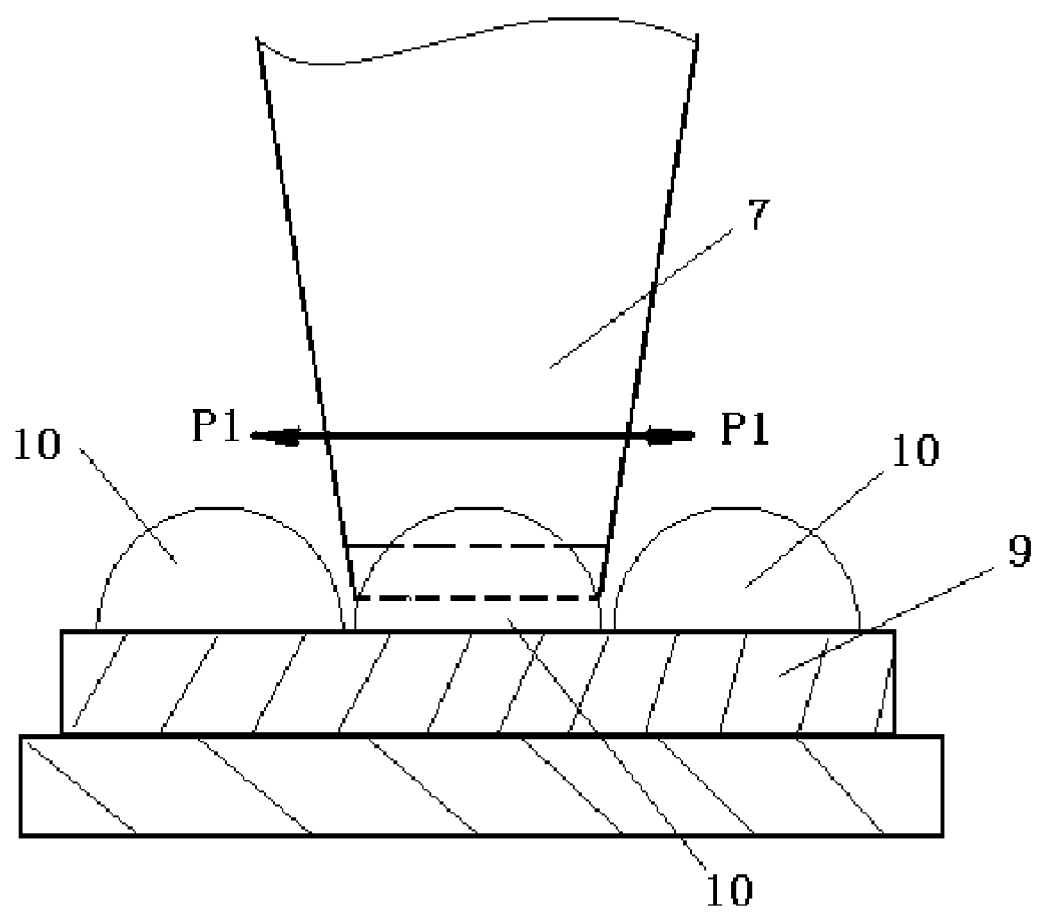
FIG. 5 is the planar structure schematic diagram of another problem in principle that an existing test device has.

Please refer to FIG. 1, FIG. 2 and FIG. 3. Disclosed in the FIG. 1, FIG. 2 and FIG. 3 is a shearing force test device, comprising a substrate 4 capable of moving up and down; the substrate 4 is provided with an elastomer 1 having horizontal position offset compensation thereon; the elastomer 1 having horizontal position offset compensation is provided with a free end 5 capable of moving toward or away from the substrate 4; the free end 5 is connected with a test head 12; a pressing mechanism (unshown) for fixing the test head 12 is arranged above the test head 12. After the test head 12 is accurately positioned, the free end 5 closely leans against the substrate 4 under the effect of the pressing mechanism to fix the test head 12; a micromotion mechanism 16 is arranged between the free end 5 and the substrate 4, wherein the micromotion mechanism 16 yields a gap between the substrate 4 and the free end 5 as well as the test head 12 connected to the free end 5 during the process of sensing a small contact force by the test head 12. In the present embodiment, the test head 12 comprises a force sensor 6 and an implemental push cutter 7. The micromotion mechanism 16 in the present embodiment comprises a sliding block 13 and an air bearing 14 (see FIG. 3); the sliding block 13 is movably connected with the substrate 4 (to be specific, the sliding block 13 is hung on the substrate 4); the air outlet of the air bearing 14 aligns to the back side surface of the sliding block 13. When not in use, the compressed air supply is stopped, and the air outlet of the air bearing 14 is completed sealed by the sliding block 13 under the effect of the pressing mechanism. And when in use, the pressing mechanism is disengaged; after the air bearing 14 is aerated with the compressed air, the sliding block 13, the free end 5 of the elastomer 1 having horizontal position offset compensation, and the test head 12 connected with the free end 5 are jacked up, forming a tiny gap from the substrate 4; under the constant supply of the compressed air, the gap is constantly kept, and the sliding block 13 and the test head 12 enter a no-friction vertically moving state. The small contact force can be sensed via the photoelectric sensor 15 or the strain meter 11. Once a contact is detected, the compressed air is closed, and the pressing mechanism presses the test head 12 and the sliding block 13 back onto the substrate, and fixes the test head 12 and the sliding block 13 on the substrate 4 via the great friction force between the substrate 4 and the sliding block 13, thus realizing the contact positioning action.

In the present invention, the micromotion mechanism 16 can also be a planar rolling bearing or a linear bearing. Utilizing the planar rolling bearing or linear bearing to replace the sliding block and air bearing structure is also acceptable.

In the present invention, the micromotion mechanism 16 can also be provided with a magnetic body at the free end 5, and a coil on the substrate 4 at a position opposing to the free end 5. After the coil is powered on, the magnetism generated by the coil is the same with the magnetism of the free end 5, and generates a repulsion effect on the free end 5, thus achieving the purpose of keeping the free end 5 and the test head 12 connected to the free end away from the substrate 4. After the fixed contact position is found, the coil is powered with a reverse current; the magnetic field of the coil changes direction; the free end 5 and the test head 12 connected to the free end are pressed back onto the substrate by the elastomer 1 having horizontal position offset compensation; and the pressure applied on the free end 5 and fixing the free end 5 and the test head 12 connected to the free end on the substrate is further enhanced via the magnetic force, thus improving the contact friction force.

Please refer to FIG. 2. In the embodiment of the present invention, the elastomer 1 having horizontal position offset compensation comprises an elastic arm 100 and an elastic arm 100' as well as an elastic arm 200 and an elastic arm 200' which can mutually neutralize the horizontal position offsets, wherein the elastic arm 100 and the elastic arm 100' are connected end to end to form a first U-shaped elastic arm, and the elastic arm 200 and the elastic arm 200' are connected end to end to form a second U-shaped elastic arm. The two U-shaped elastic arms are vertically placed at a distance. The first U-shaped elastic arm is connected with the test head 12 and the free end 5 of the second U-shaped elastic arm; the fixed ends 500 of the first U-shaped elastic arm and the second U-shaped elastic arm are respectively connected with a fixing block 400; the fixing block 400 is fixedly installed on the substrate 4. The outer ends of the first U-shaped elastic arm and the second U-shaped elastic arm are fixedly connected to each other via a vertical connecting beam 300. The test sensor 15 and the test tool 12 are installed on the free end 5 of the elastomer 1 having horizontal position offset compensation.

A sensing element is adhered at a position where the strain of the elastomer 1 having horizontal position offset compensation is concentrated, the sensing element being used to sense the deformation of the elastomer 1 having horizontal position offset compensation and control the magnitude of the contact force so as to adapt the contact of different soft/hard surfaces. The sensing element in the present embodiment is a strain meter 11 or a photoelectric sensor 15 which can also be used at the same time to achieve a better effect.

When in use, the device has an XY axes moving platform and a Z axis moving platform. The elastomer 1 having horizontal position offset compensation is fixedly installed on the substrate via the fixing block 400 by using bolts; the substrate 4 is installed on the Z axis, and can vertically move along the Z axis. The free end 5 is firmly connected with the test head 12; the micromotion mechanism 16 keeps a tiny gap between the free end 5 and the substrate 4, such that the free end 5 and the force sensor 6 connected to the free end can move freely up and down together with the implemental push cutter 7, and naturally fall to achieve balance under the effects of the elastic force of the elastomer 1 having horizontal position offset compensation and gravity of the force sensor 6 and the implemental push cutter 7. A sensing element for sensing the elastic deformation, such as the strain meter 11, is adhered at a position where the strain of the elastomer 1 having horizontal position offset compensation is concentrated. Driven by the Z axis, the substrate 4 moves towards the plane attached by the to-be-tested welded object; when the implemental push cutter 7 contacts the plane 9 attached by the to-be-tested welded object, because the elastomer 1 having horizontal position offset compensation is a U-shaped elastic arm formed by end to end connecting two parallelly arranged elastic arms, the two arms generate symmetrical deformations which are different as the contact force changes. When the free end of the elastomer 1 having horizontal position offset compensation vertically displaces, the elastic arms 100, 100' deform and mutually neutralize the horizontal position offsets, and the elastic arms 200, 200' can also deform and mutually neutralize the horizontal position offsets, therefore no offset will occur to the position of the contact point, and no horizontal offset P1 will occur to the fixed position within the elastic deformation range of the elastomer 1 having horizontal position offset compensation. The strain meter 11 adhered at a position where the strain of the elastomer 1 having horizontal position offset compensation is concentrated, transmits different magnitudes of electric signals to a signal acquisition system under the effect of different deformations of the elastomer 1 having horizontal position offset compensation. The system sets parameters via software, stops the movement of the Z axis to eliminate the thrust force of the micromotion mechanism 16 to the free end 5 according to the instruction of different magnitudes of electric signals, and simultaneously drives the pressing mechanism to closely press the free end 5 of the elastomer 1 having horizontal position offset compensation by using a mechanical force, so as to complete contact sensing and realize positioning. That is to say, the problem of horizontal offset of the fixed contact position is thoroughly eliminated, thus strictly satisfying the requirements for precise positioning. Furthermore, different magnitudes of contact forces can be conveniently adjusted via the software by processing the electric signals transmitted by the strain meter 11, and the adjustment of the contact forces will not bring the offset of the fixed position. After completing the contact positioning, the system controls to substrate 4 to rise by a preset height such as a few um, and the XY axes drives the to-be-tested welded object 10 and the plane 9 attached by the to-be-tested welded object to move towards the implemental push cutter 7 to conduct shearing force test. The signal acquisition system starts to acquire the signal change of the force sensor 6 during the whole test process. After the shearing force test is completed, the substrate is driven by the Z axis to rise by a safe height.

The elastomer 1 having horizontal position offset compensation can be designed into a plurality of shapes so as to obtain different elasticity coefficients. For example, the elastic arms for mutually neutralizing the horizontal position offset can be placed vertically or horizontally; the key is that the design must ensure the horizontal position offsets to be reverse in direction when the deformation occurs during contact sensing, so that the horizontal position offsets can be mutually neutralized to ensure that no horizontal offset will occur to the position of the contact point.

The pressing mechanism can employ a plurality of structure modes such as electromagnet pressing, cylinder pressing and the like which will not be detailed herein. The XYZ moving platforms, the servo control system, and the data acquisition system and software will not be detailed herein either.

What is claimed is:

1. A shearing force test device comprises a substrate mounted with an elastomer having a free end capable of moving toward or away from the substrate, the free end being connected with a test head, wherein a micromotion mechanism is arranged between the free end and the substrate, wherein the micromotion mechanism yields a gap between the substrate and the free end as well as the test head connected to the free end during the process of sensing a small contact force by the test head.

2. The shearing force test device according to claim 1, wherein the micromotion mechanism comprises a sliding block and an air bearing;
   wherein the sliding block is movably connected with the free end, and is flatly pressed on the substrate; the air bearing is arranged in the back of the sliding block; and the air outlet of the air bearing aligns to the back side surface of the sliding block.

3. The shearing force test device according to claim 2, wherein a sensing element is adhered at a position where the strain of the elastomer having horizontal position offset compensation is concentrated, the sensing element being used to sense the deformation of the elastomer and control the magnitude of the contact force so as to adapt the contact of different soft/hard surfaces.

4. The shearing force test device according to claim 3, wherein the sensing element is a strain meter or a photoelectric sensor.

5. The shearing force test device according to claim 1, wherein the micromotion mechanism is a planar rolling bearing or a linear bearing.

6. The shearing force test device according to claim 5, wherein a sensing element is adhered at a position where the strain of the elastomer having horizontal position offset compensation is concentrated, the sensing element being used to sense the deformation of the elastomer and control the magnitude of the contact force so as to adapt the contact of different soft/hard surfaces.

7. The shearing force test device according to claim 6, wherein the sensing element is a strain meter or a photoelectric sensor.

8. The shearing force test device according to claim 1, wherein the micromotion mechanism is provided with a magnetic body at the free end, and a coil on the substrate at a position opposing to the free end; after the coil is powered on, the magnetism generated by the coil is the same with the magnetism of the free end, thus having a repulsion action on the free end.

9. The shearing force test device according to claim 8, wherein a sensing element is adhered at a position where the strain of the elastomer having horizontal position offset compensation is concentrated, the sensing element being used to sense the deformation of the elastomer and control the magnitude of the contact force so as to adapt the contact of different soft/hard surfaces.

10. The shearing force test device according to claim 9, wherein the sensing element is a strain meter or a photoelectric sensor.

11. The shearing force test device according to claim 1, wherein a sensing element is adhered at a position where the strain of the elastomer having horizontal position offset compensation is concentrated, the sensing element being used to sense the deformation of the elastomer and control the magnitude of the contact force so as to adapt the contact of different soft/hard surfaces.

12. The shearing force test device according to claim 11, wherein the sensing element is a strain meter or a photoelectric sensor.

* * * * *